(12) United States Patent
Abbadie et al.

(10) Patent No.: US 7,579,309 B2
(45) Date of Patent: Aug. 25, 2009

(54) METHODS FOR CHARACTERIZING DEFECTS ON SILICON SURFACES AND ETCHING COMPOSITION AND TREATMENT PROCESS THEREFOR

(75) Inventors: Alexandra Abbadie, Le Versoud (FR); Jochen Maehliss, Karlstein (DE); Bernd Kolbesen, Bad Homburg (DE)

(73) Assignee: S.O.I.Tec Silicon on Insulator Technologies, Bernin (FR)

( * ) Notice: Subject to any disclaimer, the term of this patent is extended or adjusted under 35 U.S.C. 154(b) by 73 days.

(21) Appl. No.: 11/749,358

(22) Filed: May 16, 2007

(65) Prior Publication Data
US 2008/0099718 A1 May 1, 2008

(30) Foreign Application Priority Data
Oct. 31, 2006 (EP) ................... 06291711

(51) Int. Cl.
C11D 7/26 (2006.01)
C11D 7/08 (2006.01)
C11D 7/10 (2006.01)
H01L 21/00 (2006.01)
B08B 7/00 (2006.01)

(52) U.S. Cl. ............ 510/175; 510/176; 438/8; 438/494; 438/745; 438/752; 438/753; 438/689; 134/1.3; 134/41; 134/42

(58) Field of Classification Search .......... 510/175, 510/176; 438/8, 494, 745, 752, 753, 689; 134/1.3, 41, 42
See application file for complete search history.

(56) References Cited

U.S. PATENT DOCUMENTS 2,619,414 A 1/1952 Heidenreich .......... 41/42
5,714,407 A * 2/1998 Maeno et al. .......... 438/701
5,985,689 A 11/1999 Gofuku et al. .......... 439/59
6,042,739 A 3/2000 Itoh .......... 216/96
6,410,436 B2 * 6/2002 Yamagata et al. .......... 438/689
6,656,022 B2 * 12/2003 Ota et al. .......... 451/41
2005/0009207 A1 * 1/2005 Vos et al. .......... 438/1
2006/0089280 A1 * 4/2006 Vos et al. .......... 510/175
2007/0256705 A1 * 11/2007 Abbadie et al. .......... 134/3
2008/0124938 A1 * 5/2008 Abbadie .......... 438/753

FOREIGN PATENT DOCUMENTS

DE 102005012356 10/2005
EP 1 734 572 A1 12/2006
WO WO 2004/106227 A1 12/2004

OTHER PUBLICATIONS

Pugh, E.N., et al., "Etching of Abraded Germanium Surfaces with CP-4 Reagent", Journal of the Electrochemical Society, 1962, 109, 5, 409-412.*
Kesner, Miri, Bromine and Bromine Compounds from the Dead Sea, Israel: Products in the Service of People, Weizmann Institute of Science, Jan. 30, 2005, pp. 161-205.*
J. Mähliβ et al., "Development of Chromium-free Etching Solutions for Application on SOI and sSOI," J.W.G.-University, Franfurt/Main, Germany, SOITEC, Bernin France, 1 page.
F. Secco d' Aragona, "Dislocation Etch for (100) Planes in Silicon," J. Electrochem. Soc.: Solid-State Science and Technology, vol. 119, No. 7, Jul. 1972, pp. 948-951.
W.C. Dash, "Copper Precipitation on Dislocations in Silicon," Journal of Applied Physics, vol. 27, No. 10, Oct. 1956, pp. 1193-1195.

* cited by examiner

*Primary Examiner*—Douglas Mc Ginty
(74) *Attorney, Agent, or Firm*—Winston & Strawn LLP

(57) ABSTRACT

The present invention relates to a method for characterizing defects on silicon surfaces, such as silicon wafers, a method for treating silicon surfaces with an etching solution, and an etching solution to be employed in the treating and defect characterization of such silicon wafer surfaces.

21 Claims, 7 Drawing Sheets

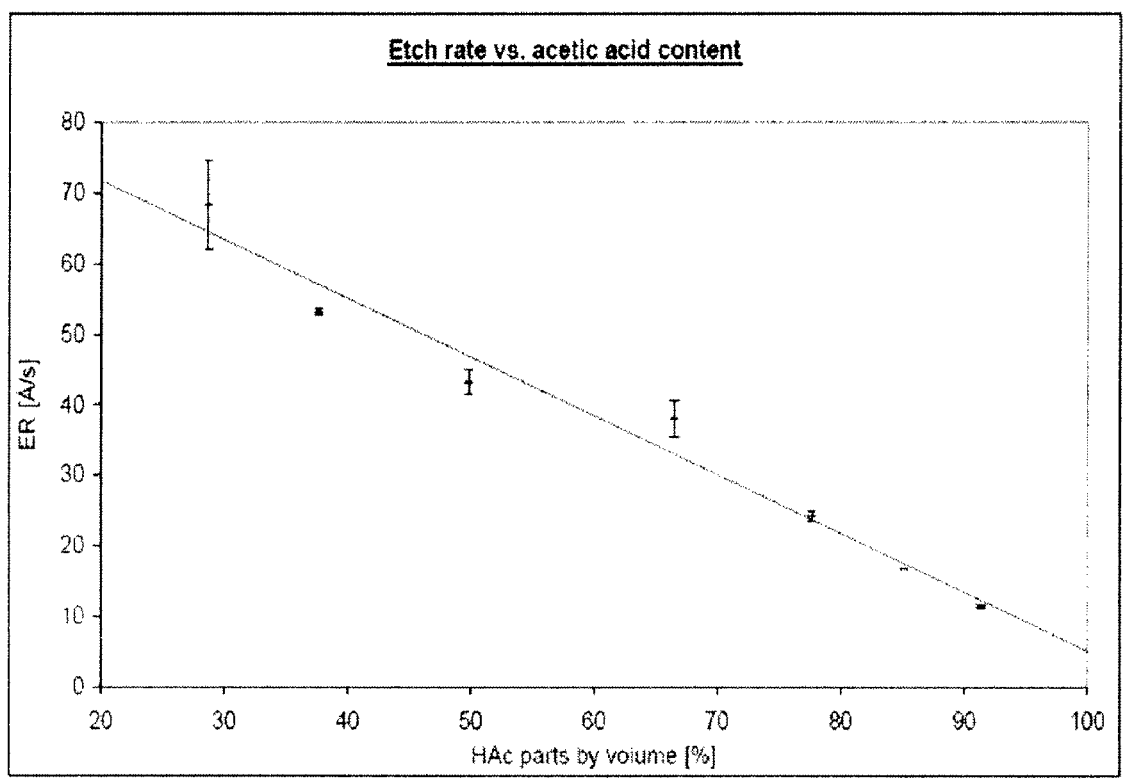
Figure 1: Etch rate on SOI vs the acetic acid content (in volume %)

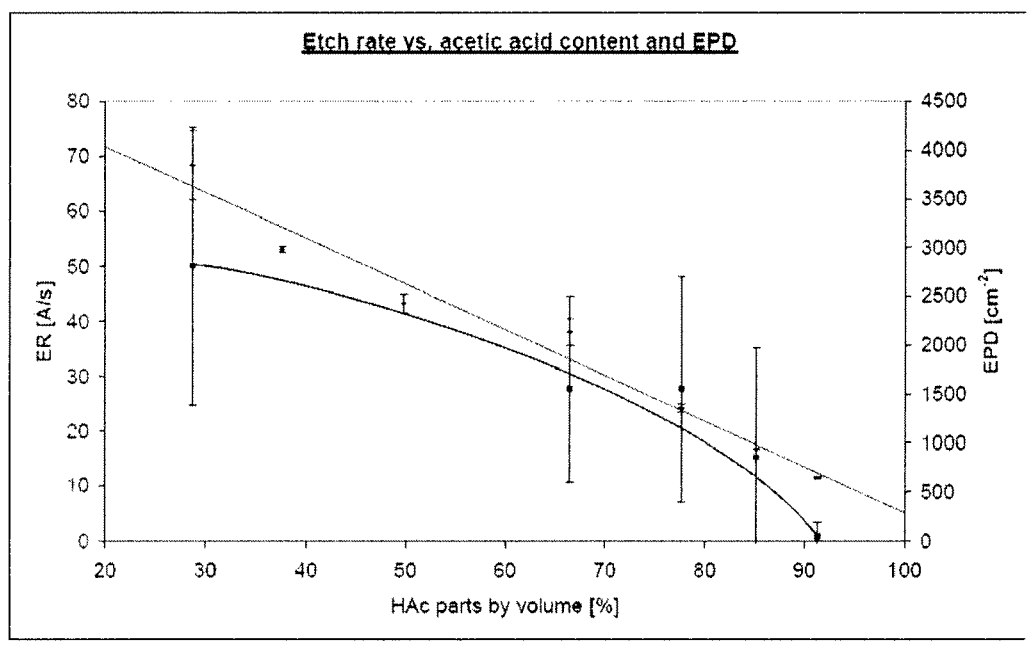
Figure 2: Evolution of the etch rate vs the acetic acid content and its influence in terms of etch pits densities (EPD) in $cm^{-2}$.

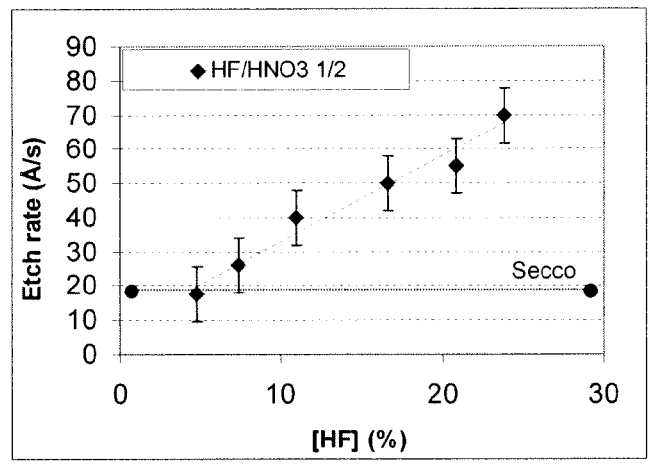

Figure 3: Variation of the etch rate (Å/s) as a function of the HF concentration, for a ratio $HF/HNO_3$ 1/2 (acid acetic and HF are variable).

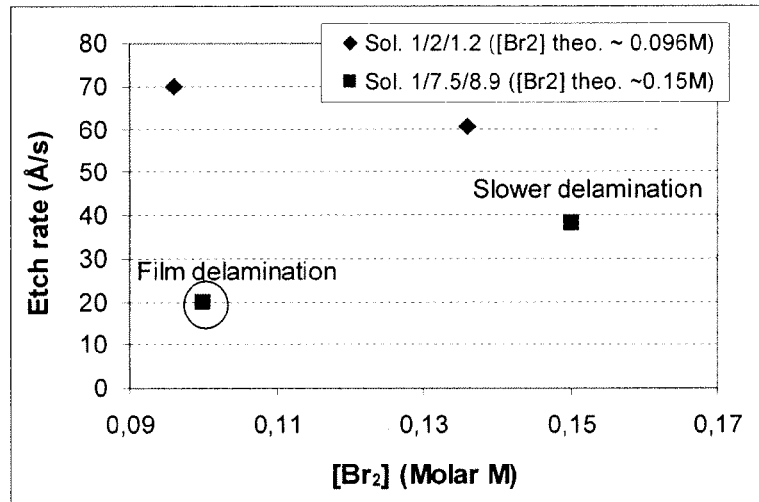

Figure 4: Etch rate (Å/s) on SOI as a function of $Br_2$ concentration (Molar). The expected $Br_2$ concentrations (theorical) are reported for each solution depending on its volumetric ratios. The experiments were performed at room temperature.

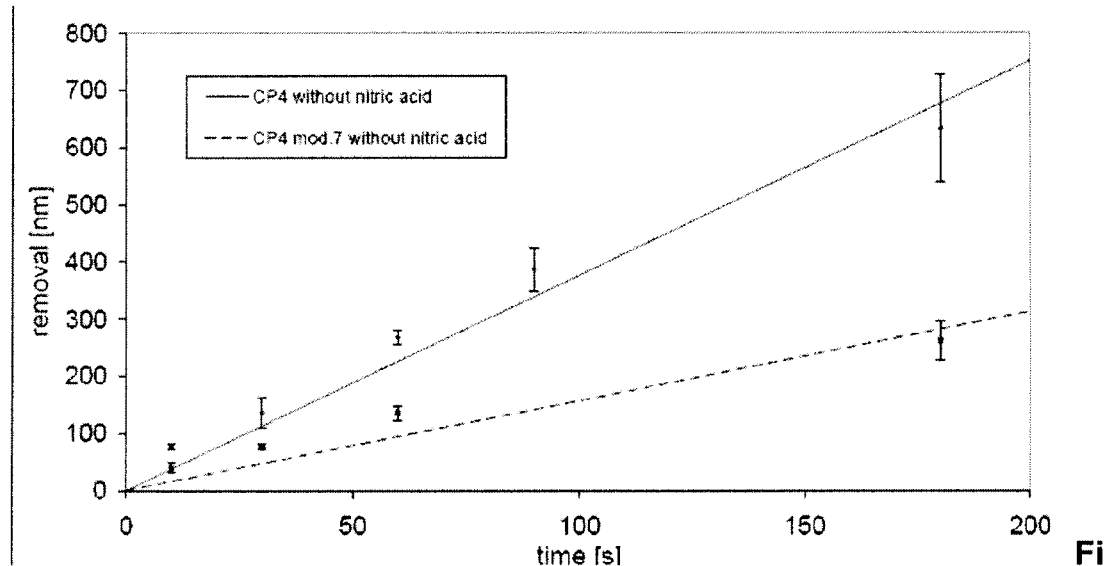
Figure 5: Removal (in nm) of a piece of SOI as a function of time (s) using a CP4 modified solution in accordance with the present invention (mod.7 corresponding to 1/2/17.5 ratio of HF/HNO3/CH3COOH).
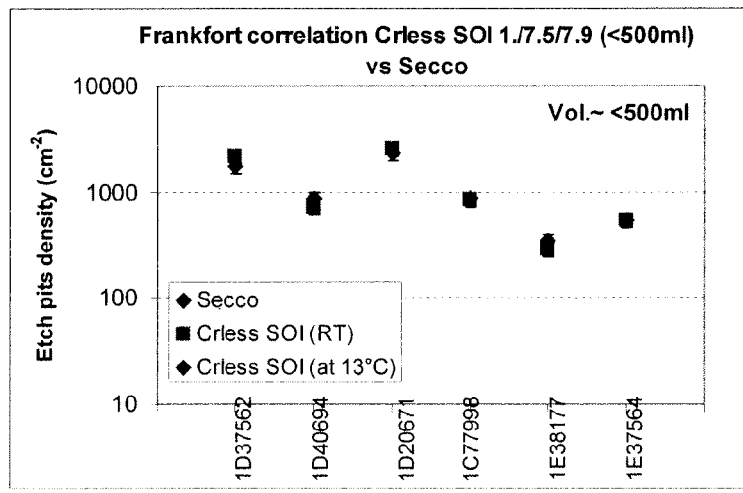
Figure 6: Etch pits density ($cm^{-2}$) for different pieces of SOI wafers after etching in accordance with the present invention and Secco etching, at room temperature.

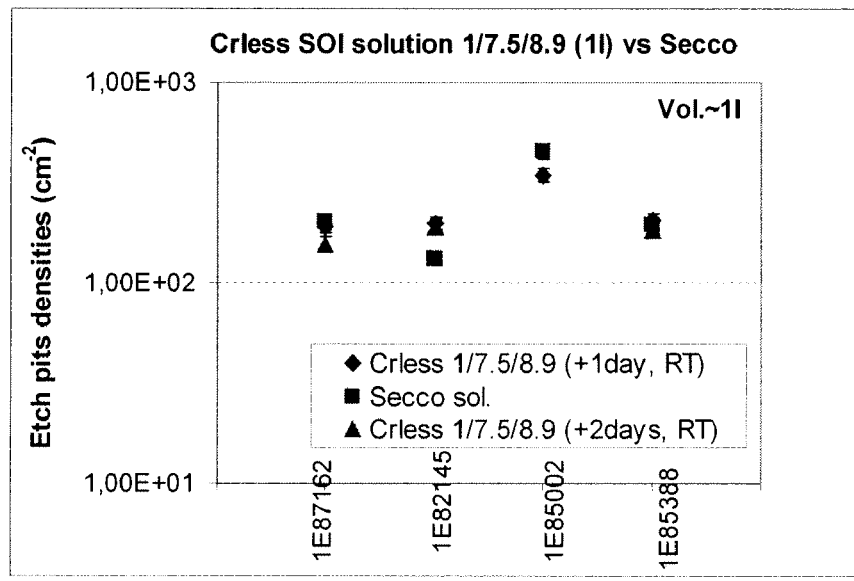
Figure 7: Etch pits density (cm$^{-2}$) for different pieces of SOI wafers after etching in accordance with the present invention (volume ~ 1liter) and Secco etching, at room temperature.

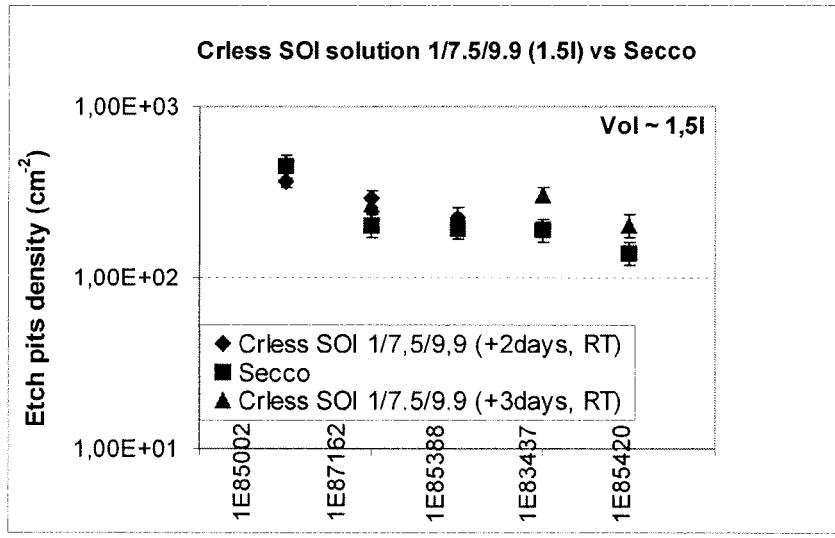
Figure 8: Etch pits density (cm$^{-2}$) for different pieces of SOI wafers after etching in accordance with the present invention (volume ~ 1.5 liters) and Secco etching, at room temperature.
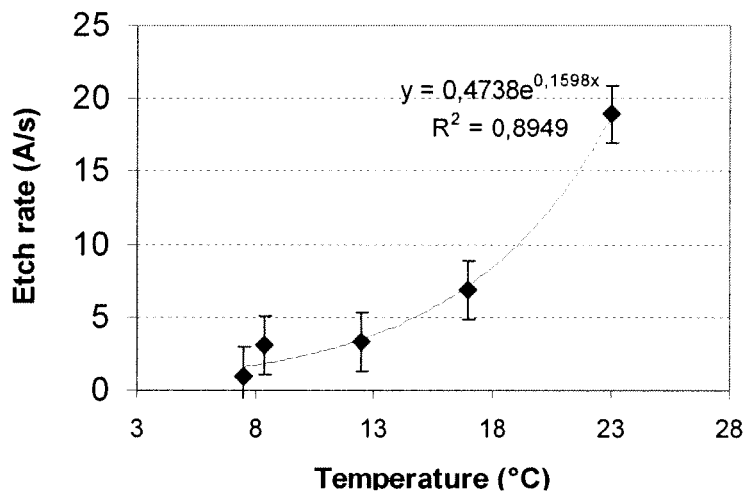
Figure 9: Evolution of the etch rate (Å/s) as a function of the temperature (from room temperature down to 5°C) for an etching solution of the present invention.

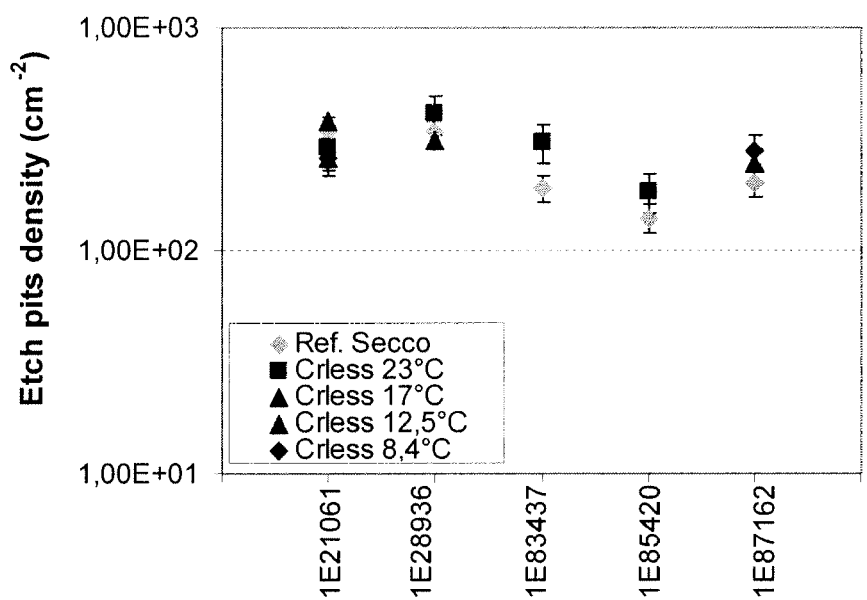
Figure 10: Etch pits density (cm-2) for different pieces of SOI wafers after etching at different temperature (from room temperature down to 8°C) in accordance with the present invention and Secco etching at room temperature.

US 7,579,309 B2

METHODS FOR CHARACTERIZING DEFECTS ON SILICON SURFACES AND ETCHING COMPOSITION AND TREATMENT PROCESS THEREFOR

BACKGROUND

The present invention relates to a method for characterizing defects on silicon surfaces, in particular silicon wafers, a method for treating silicon surfaces with an etching solution and the etching solution to be employed in the method and process of the present invention.

Crystalline defects in substrate for microelectronic devices are highly undesirable as they have a negative impact on the functionality and reliability of integrated circuits, formed using the substrates, such as wafers, in particular silicon-on-insulator (SOI) type wafers. The typical approach for identifying crystalline defects and thereby characterizing the quality of substrate surfaces is the use of so-called structural etching solutions. These etching solutions, due to the dependency of the etch rate from crystalline structures, can identify crystalline defects, since crystalline defects give rise to either hillocks or etch pits after application of the structural etching solution.

Various etching solutions have been proposed for silicon surfaces which require typically the presence of strong oxidants.

W. C. Dash in the Journal of Applied Physics, vol. 27, no. 10, pp. 1193-1195 (1956) discloses a further etched solution able to reveal defects on semiconductor substrates, consisting of hydrofluoric acid, nitric acid and acetic acid. While this solution is able to etch semiconductor substrates, including silicon substrates, the etching solution according to Dash is not able to differentiate between different types of defects and furthermore does not provide a satisfactory etch rate.

U.S. Pat. No. 2,619,414 discloses a further chemical etchant to be applied on semiconductor surfaces to improve their electrical characteristics. The chemical etchant disclosed in that patent comprises acetic acid, nitric acid, hydrofluoric acid and bromine. The drawback of the composition of that patent is the use of bromine, which is highly instable and volatile, so that the chemical etchant according to this prior art reference can only be stored for a very short time in the dark at low temperatures and can be handled only under ventilation, since bromine evaporates from the composition. Although bromine is not as toxic as chromate or dichromate, precautionary measures nevertheless have to be taken when using that chemical as an etchant.

In view of the progress in semiconductor industry, involving in particular the decrease of the minimum feature sizes used to fabricate integrated circuits, the introduction of new substrate materials, such as silicon-on-insulator (SOI) or strained-silicon-on-insulator (sSOI), improved methods for quality characterization are required, in particular with respect to the following features:

Satisfactory etch rates, so that even thin substrates can be etched with sufficient control of etch rate/etch time/removed surface thickness.

Etch sensitivity, i.e. the possibility to detect different types of defects (such as D defects corresponding to agglomerates of vacancies and oxygen precipitates), most preferably identifying different types of defects after one type of etching treatment.

Reduction of health risks and environmental problems by using suitable components for the etching composition, without sacrificing the desired properties, etch rate, etch sensitivity etc.

Stability of the etching composition, so that same can be stored for a certain period of time and can be handled without highly elaborated safety measures.

Thus, there is a need for improved etching compositions and etching processes for such purposes and these are now provided by the present invention.

SUMMARY OF THE INVENTION

The present invention relates to a method for characterizing defects on silicon surfaces. It also relates to an etching solution for treating semiconductor surfaces that contain such defects.

The etching solution according to the present invention provides for an etch rate which is low enough so that even thin semiconductor substrates can be etched, without sacrificing the desired etching properties, such as formation of well developed etch pits, facilitating surface characterization. Due to the relative high acetic acid content in a preferred etching solution highly satisfactory homogeneous surfaces can be obtained. The use of bromates and bromides also alleviate the necessity to employ bromine as a starting ingredient.

With an etching solution in accordance with the present invention, it is possible to reveal surface defects on semiconductor substrates, even on thin substrates, such as SOI or sSOI substrates.

BRIEF DESCRIPTION OF THE DRAWING FIGURES

FIG. 1 shows a graph displaying the dependency of the etch rate as a function of the content of acetic acid.

FIG. 2 shows a graph showing a correlation between etch rate, acetic acid content and etch pit density.

FIG. 3 displays a graph showing the correlation between etch rate and concentration of hydrofluoric acid.

FIG. 4 shows the influence of bromine content on etch rates.

FIG. 5 shows the influence of nitric acid on material consumption and so its necessity for etch pits delineation.

FIG. 6 represents a comparison of etch pit densities as obtained with etching compositions in accordance with the present invention, compared with a composition in accordance with the prior art reference Secco.

FIGS. 7 and 8 likewise display a similar comparison, employing etching compositions in accordance with the present invention which had been stored for several days.

FIG. 9 shows the evolution of the etch rate with decreased temperature (down to 8° C.).

FIG. 10 plots the comparison of EPD (Etch Pits Densities) with etching composition in accordance with the present invention from room temperature down to 8° C., compared to the Secco reference.

In the Figures etching solutions in accordance with the present invention are also designated Crless SOI x/y/z, with x/y/z indicating the molar ratio $HF/HNO_3$/acetic acid.

DETAILED DESCRIPTION OF THE PREFERRED EMBODIMENTS

The present invention will be first described in connection with the etching solution. The preferred embodiments discussed here below however also apply with respect to the methods of the present invention, unless otherwise stated.

One aspect of the present invention is related to an etching solution for treating semiconductor surfaces. The etching solution in accordance with the present invention comprises hydrofluoric acid, nitric acid, acetic acid, an alkali bromide and an alkali bromate as disclosed herein. Preferably the bromide and bromate compounds are sodium bromide and sodium bromate, repectively. The components of the etching solution in accordance with the present invention are explained in further detail below:

1.) The hydrofluoric acid to be employed in accordance with the present invention preferably is an aqueous solution of HF with a concentration of above 30%, preferably above 40%, more preferably above 45%, such as about 49%.

2.) Furthermore, the etching solution in accordance with the present invention comprises nitric acid. The nitric acid to be employed in accordance with the present invention again preferably is an aqueous solution, typically showing a nitric acid concentration of above 50%, more preferably above 60%, and in particular above 65%, such as about 70%.

3.) The acetic acid to be employed in accordance with the present invention preferably is a pure acetic acid, such as an acetic acid commercially available as glacial acetic acid having an acetic acid content of about 99%.

4.) The alkali bromide and the alkali bromate are preferably sodium bromide and sodium bromate respectively, although also other alkali salts, such as potassium salts may be employed.

Preferably the etching solution in accordance with the present invention comprises the components identified above, i.e., the etching solution is an aqueous mixture, or solution, of the components mentioned herein.

These components of the etching solution in accordance with the present invention may be present in the overall mixture in the following amounts:

Hydrofluoric acid: about 2 to 30 vol %, preferably 10 to 25 vol %, more preferably 15 to 25 vol %, calculated on the basis of an aqueous HF having a concentration of about 49%.

Nitric acid: addition amounts so that the molar ratio HF/HNO$_3$ is from about 1:2 to about 1:15, preferably about 1:2 to about 1:10, more preferably about 1:5 to about 1:8, in particular about 1:7.5. This amount is generally between about 4 to 60%.

Acetic acid: about 20 to 90 vol %, based on the overall composition of the etching solution, preferably 30 to 90 vol %, more preferably 50 to 90 vol %, calculated on the basis of an acetic acid having a concentration of 99%.

Ratio HF/CH$_3$COOH: preferably adjusted to a molar ratio from about 1:5 to about 1:15, preferably 1:7 to 1:10, in particular 1:7.9

Alkali bromide and alkali bromate: ratio of bromide to bromate of about 2:1 to 10:1 and preferably about 5:1, so that a molar bromine concentration, resulting from the reaction of bromate and bromide according to the equation NaBrO$_3$+ 5NaBr+6H$^+$=3Br$_2$+3H$_2$O+6Na$^+$, amounts from about 0.02 to about 0.5, preferably about 0.04 to about 0.3, more preferably about 0.048 to about 0.288.

The etching solution in accordance with the present invention may be prepared by simply mixing the components identified above in the desired ratio, typically using conventional safety measures. The order of addition of the components is not critical and the components usually are mixed within a stirred vessel. The composition as obtained may be stored without loss of etching activity for several days, typically under cool conditions (i.e., about 0 to 10° C.).

The use of an etching solution in accordance with the above is highly satisfactory. The etching solution as defined above provides for an etch rate which is low enough so that even thin semiconductor substrates can be etched, without sacrificing the desired etching properties, such as formation of well developed etch pits, facilitating the surface characterization.

Due to the relative high acetic acid content in the preferred etching solution in accordance with the present invention, highly satisfactory homogeneous surfaces can be obtained and the use of bromate and bromide alleviates the necessity to employ bromine as a starting ingredient.

With an etching solution in accordance with the present invention, it is possible to reveal surface defects on semiconductor substrates, even on thin substrates, such as SOI or sSOI substrates. The shape of revealed etch pits are mainly conic shallow pits and observable as a round mark (spot) after the etching treatment (see FIG. 9). The etching solution in accordance with the present invention, depending from the actual composition, provides etch rates of 3 to 70 Å/sec, so that highly satisfactory total etch times can be achieved even when using thin substrates, such as SOI substrates where it is required to remove about 500 to 600 Å of the initial surface.

F. Secco describes in the Journal of Electrochemical Society, 119, no. 7, pp. 948-951 (1972), an etching solution for revealing etch pits in silicon, consisting of a mixture of hydrofluoric acid and aqueous alkali dichromate. The alkali chromate acts as oxidizing agent while the hydrofluoric acid dissolves the oxidation product, namely silicon dioxide. However, chromates and, in particular, dichromates are highly toxic due to their ability to interact with cells and DNA. This article is hereby incorporated by referenced in its entirety.

In this respect, it furthermore has been shown, using the etching solution in accordance with the Secco reference, that the solution in accordance with the present invention enables a highly satisfactory and more reliable identification of defects, as evidenced by the very similar etch pit densities obtained. Additionally, these experiments show that the etching solution in accordance with the present invention may even be stored for at least up to 3 days at room temperature without sacrificing the etch properties (see FIGS. 4 to 8).

Overall, it is therefore readily apparent that the etching solution in accordance with the present invention enables a vast improvement compared with the etching compositions as known so far from the prior art. Various combinations of these components can be devised by skilled artisans having this disclosure before them.

For example, a preferred etching solution comprises:
hydrofluoric acid in an amount of about 2 to 30%;
nitric acid in an amount of about 4 to 60%;
acetic acid in an amount of about 20 to 90%; and
a further etchant of an alkali bromide or an alkali bromate in an amount sufficient to enhance etching performance of the solution.

A more preferred etching solution comprises:
hydrofluoric acid in the form of a is an aqueous solution of HF having a concentration of above 30%, and is present in an amount of about 10 to 25%;
nitric acid in an amount of about 4 to 60% in an amount to provide a molar ratio of hydrofluoric acid/nitric acid of from about 1:2 to about 1:15;
acetic acid in an amount of about 50 to 90% and in an amount sufficient to provide a molar ratio of hydrofluoric acid and acetic acid of from about 1:5 to about 1:15; and
a further etchant of an alkali bromide and an alkali bromate in an amount sufficient to enhance etching performance of the solution, wherein the alkali bromide and alkali bromate are each present and in sufficient amounts to provide a molar ratio of alkali bromide/alkali bromate of from about 2:1 to 10:1 or wherein the alkali bromide and alkali bromate are each present and in sufficient amounts to provide a molar bromine concentration, resulting from the reaction of bromate and bromide according to the equation $NaBrO_3+5NaBr+6H^+ \rightarrow 3Br_2+3H_2O+6Na^+$, that is from about 0.02 to about 0.5.

Of course, other combinations of these components can be utilized depending upon the substrate to be etched, and the preferred embodiments in accordance with the present invention are further illustrated by the performance shown in the appended Figures discussed herein.

FIG. 1 shows that the etch rate in particular can be controlled by adjusting the acetic acid content. Higher etch rates are obtained with low acetic acid contents. Too high contents of acetic acid however also may be detrimental in that delamination could be induced. FIG. 2 further shows that too high contents of acetic acid also may be detrimental in that fewer defects are identified, as evidenced by the lower EPD values. FIG. 2 also shows that the ratio $HF/HNO_3$ may be adjusted in accordance to the low etch rate and enables at the same time the formation of etch pits. In particular, a ratio $HF/HNO_3$ 1/7.5 is preferred to keep a good compromise between etching and defects delineation. FIG. 3 shows that etch rates may also be adjusted by adjusting the HF content. Higher HF contents usually give rise to higher etch rates. FIG. 4 also shows that the molar $Br_2$ concentration, resulting from the reaction of bromide and bromate, enables a control of the etch rate. FIG. 5 displays that the nitric acid is needed for the surface oxidation and that the content has to be adjusted to enable a control of the etch rate and the etch sensitivity (ratio preferred $HF/HNO_3 > \frac{1}{2}$). No etch pits could be detected without nitric acid, confirming that the capability for making defects visible is due to the presence of nitric acid.

FIGS. 6 to 8 show that the etching solution in accordance with the present invention reveals very similar EPD, compared with the standard Secco composition, even after storage for 1 to 3 days, a storage not possible with the composition disclosed in U.S. Pat. No. 2,619,414.

FIG. 9 shows that the etch rate of the solution can also be controlled by decreasing the temperature of the mixed solution. This cooled etch solution can then typically be applied for etching of thin SOI surfaces (from 0 to 800 Å), enlarging the range of potential substrates.

FIG. 10 shows that the etching composition in accordance with the present invention reveals very similar EPD even at lower temperature than the room temperature (from 23° C. to 8° C.), compared with the standard Secco composition. Decreasing the temperature of the solution for thin film application does not influence the EPD.

The experiments as illustrated in FIGS. 9 and 10 show one further important aspect in accordance with the present invention. Without sacrificing the EPD, the reliability of the etching process, the etching solution in accordance with the present invention may be employed at rather low temperatures with highly efficient etching results, which allows for greater control of the etching process. Due to the rather low etching rates at low temperature, it is in particular possible to etch, with a sufficiently high degree of control, very thin substrates without endangering the overall integrity of the substrate to be treated.

It is accordingly possible to conduct etching over a wide range of temperatures, such as from 5 to 50° C., preferably 5 to 25° C., and depending from the circumstances either at low temperatures such as from 5 or 8 to 15° C., or at higher temperatures, such as from 20 to 25° C., in certain embodiments preferably at 23° C.

Further, as already outlined above, the present invention provides a method for characterizing defects on silicon surfaces as well as a process for etching silicon surfaces, which both comprise a step of etching a silicon surface with an etching solution as defined herein.

In the method as well as the process in accordance with the present invention the silicon surfaces may be surfaces of semiconductor substrates, such as conventional silicon substrates or preferably SOI or sSOI materials.

These substrates may be subjected to any conventional pretreatment, and after application of the etching solution in accordance with the present invention, the substrates again may be subjected to conventional post-treatments such as washing, drying etc. as required.

As indicated above, the use of the etching solution in accordance with the present invention enables superior control of the etch rate together with highly satisfactory etch results, i.e., highly reliable detection of defects on the treated surface.

The present invention accordingly proves that it is possible to use the etching solution that has been described in an industrial etching process in replacement of the reference Secco solution.

What is claimed is:

1. An etching solution, comprising, in volume percent:
   hydrofluoric acid in an amount of about 2 to 30%;
   nitric acid in an amount of about 4 to 60%;
   acetic acid in an amount of about 20 to 90%; and
   a further etchant of an alkali bromide or an alkali bromate in an amount sufficient to enhance etching performance of the solution.

2. The etching solution of claim 1 wherein the hydrofluoric acid and nitric acid are present in amounts sufficient to provide a molar ratio of hydrofluoric acid/nitric acid of from about 1:2 to about 1:15.

3. The etching solution of claim 2, wherein the hydrofluoric acid and acetic acid are present in amounts sufficient to provide a molar ratio of hydrofluoric acid and acetic acid of from about 1:5 to about 1:15.

4. The etching solution of claim 1, wherein the alkali bromide is sodium bromide or the alkali bromate is sodium bromate.

5. The etching solution of claim 1, wherein the alkali bromide and alkali bromate are each present and in sufficient amounts to provide a molar ratio of alkali bromide/alkali bromate of from about 2:1 to 10:1.

6. The etching solution of claim 1 wherein the alkali bromide and alkali bromate are each present and in sufficient amounts to provide a molar bromine concentration, resulting from the reaction of bromate and bromide according to the equation $NaBrO_3+5NaBr+6H^+ \rightarrow 3Br_2+3H_2O+6Na^+$, that is from about 0.02 to about 0.5.

7. An etching solution, consisting essentially of, in volume percent:
   hydrofluoric acid in an amount of about 2 to 30%;
   nitric acid in an amount of about 4 to 60%;
   acetic acid in an amount of about 20 to 90%; and
   a further etchant of an alkali bromide or an alkali bromate in an amount sufficient to
   enhance etching performance of the solution,
   wherein the alkali bromide and alkali bromate are each present and in sufficient amounts to provide a molar bromine concentration, resulting from the reaction of bromate and bromide according to the equation $NaBrO_3+5NaBr+6H^+ \rightarrow 3Br_2+3H_2O+6Na^+$, that is from about 0.02 to about 0.5;
   wherein the hydrofluoric acid is an aqueous solution of HF having a concentration of above 30%, and is present in an amount of about 10 to 25%;
   the nitric acid is present in an amount to provide a molar ratio of hydrofluoric acid/nitric acid of from about 1:2 to about 1:15; and the acetic acid is present in an amount of about 50 to 90% and in an amount sufficient to provide a molar ratio of hydrofluoric acid and acetic acid of from about 1:5 to about 1:15.

8. A method for characterizing defects on silicon surfaces, which comprises applying an etching solution according to claim 1 to a silicon surface.

9. A method for characterizing defects on silicon surfaces, which comprises applying an etching solution according to claim 2 to a silicon surface.

10. A method for characterizing defects on silicon surfaces, which comprises applying an etching solution according to claim 3 to a silicon surface.

11. A method for characterizing defects on silicon surfaces, which comprises applying an etching solution according to claim 4 to a silicon surface.

12. A method for characterizing defects on silicon surfaces, which comprises applying an etching solution according to claim 5 to a silicon surface.

13. A method for characterizing defects on silicon surfaces, which comprises applying an etching solution according to claim 6 to a silicon surface.

14. A method for characterizing defects on silicon surfaces, which comprises applying an etching solution according to claim 7 to a silicon surface.

15. The method of claim 8, wherein the silicon surface is present on a silicon layer upon an insulating substrate.

16. The method of claim 15, wherein the silicon surface comprises strained silicon, and wherein the strained silicon is upon an insulating substrate.

17. The method of claim 15, wherein the method further comprises a pretreatment of the silicon surface with hydrofluoric acid.

18. The method of claim 15, wherein the method further comprises post-treating the silicon surface by rinsing it with deionized water.

19. The method of claim 15, which further comprises visually evaluating the treated silicon surface.

20. The method of claim 8, which further comprises post-treating the silicon substrate by rinsing it with deionized water and dipping it into a hydrofluoric acid solution for a sufficient period of time to delineate defects.

21. The method of claim 8, wherein the treating of the silicon surface with an etching solution takes place at a temperature in the range of 5° C. to 25° C.

* * * * *

UNITED STATES PATENT AND TRADEMARK OFFICE
CERTIFICATE OF CORRECTION

PATENT NO. : 7,579,309 B2
APPLICATION NO. : 11/749358
DATED : August 25, 2009
INVENTOR(S) : Abbadie et al.

It is certified that error appears in the above-identified patent and that said Letters Patent is hereby corrected as shown below:

Title Page
Item (56) References Cited, U.S. Patent Documents, change the date of Pat. No. 2,619,414 A from "1/1952" to -- 11/1952 --.

Column 1
Line 13, after "Crystalline defects in", change "substrate" to -- substrates --.
Line 29, after "10, pp. 1193-1195 (1956) discloses a further", change "etched" to -- etch --.

Column 4
Line 50, after "hydrofluoric acid in the form of", delete "a is".

Signed and Sealed this
Twenty-first Day of February, 2012

David J. Kappos
*Director of the United States Patent and Trademark Office*